Figure 1:
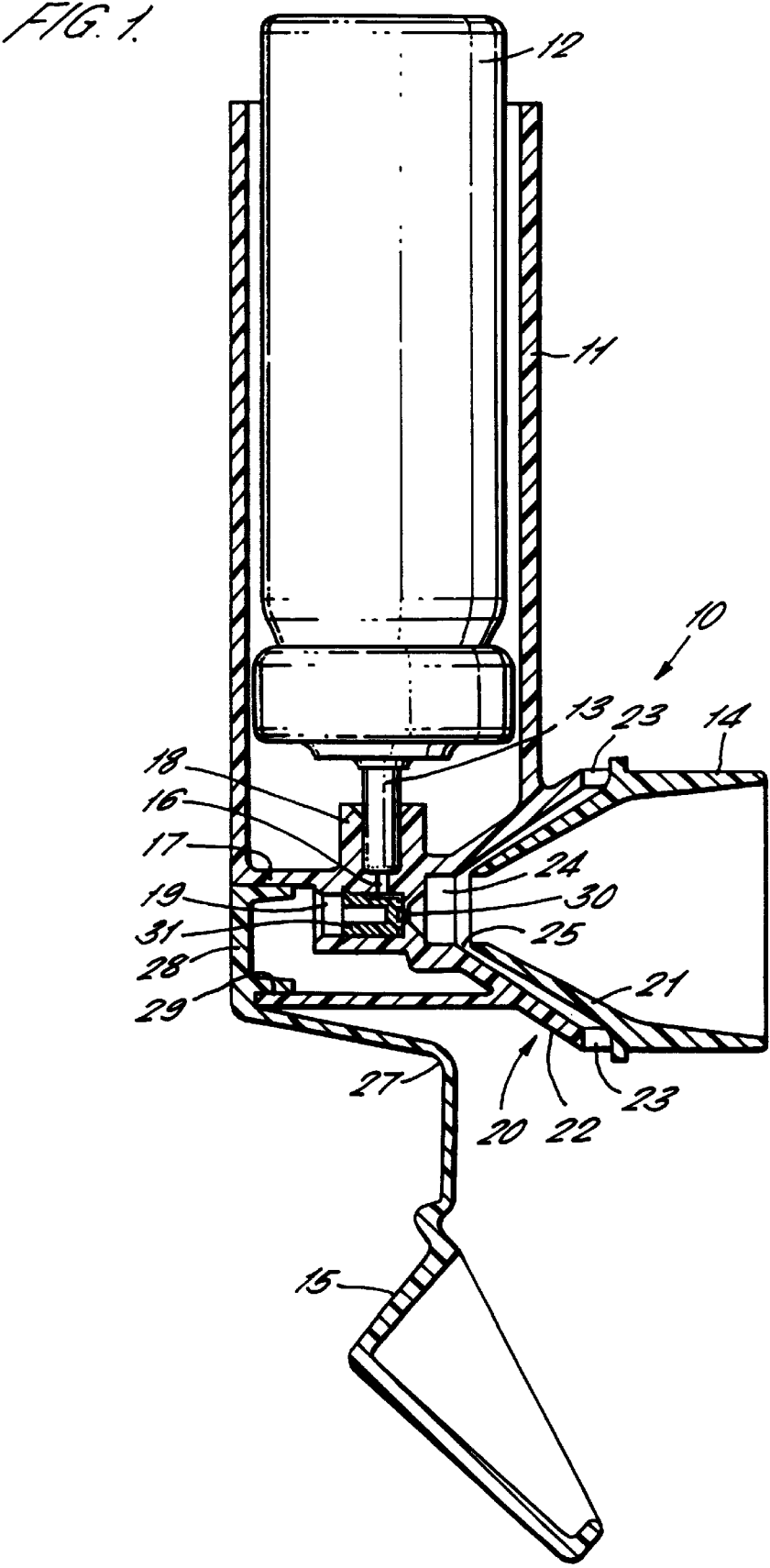

US005860416A

United States Patent [19]
Howlett

[11] Patent Number: 5,860,416
[45] Date of Patent: Jan. 19, 1999

[54] INHALERS

[75] Inventor: David Howlett, Kings Lynn, United Kingdom

[73] Assignee: Bespak plc, Norfolk, United Kingdom

[21] Appl. No.: 855,760

[22] Filed: Apr. 24, 1997

[30] Foreign Application Priority Data

Apr. 25, 1996 [GB] United Kingdom ................... 9608474

[51] Int. Cl.[6] .................................................... A61M 11/00

[52] U.S. Cl. ............................... 128/200.23; 128/200.22; 128/200.14

[58] Field of Search ......................... 128/200.14, 200.22, 128/200.23, 200.18, 203.12, 206.29; 239/337

[56] References Cited

U.S. PATENT DOCUMENTS

| | | | |
|---|---|---|---|
| 3,302,834 | 2/1967 | Alsop | 128/200.23 |
| 3,913,842 | 10/1975 | Singer | 239/337 |
| 4,940,051 | 7/1990 | Lankinen | 128/200.22 |
| 5,682,875 | 11/1997 | Blower et al. | 128/200.23 |

*Primary Examiner*—John G. Weiss
*Assistant Examiner*—Charles W. Anderson
*Attorney, Agent, or Firm*—Beveridge, DeGrandi, Weilacher & Young, LLP

[57] ABSTRACT

The invention relates to an inhaler for products such as medicaments, and particularly to an inhaler for transferring to a patient a metered dose of product contained in a pressurized dispensing container. The inhaler includes a housing adapted to receive a pressurized dispensing container, a mouthpiece, duct means for connecting an outlet of the container with the mouthpiece and air inlet means for allowing air into the inhaler for when a user applies suction to the mouthpiece. The housing also comprises a mechanical break-up component located in the duct means. The component breaks up the product as it passes along the duct means, before mixing with the air flow to effect atomization of the product. The duct means includes a chamber for receiving the mechanical break-up component, the chamber having an end wall providing a barrier between the chamber and the mouthpiece to prevent the mechanical break-up component from entering the mouthpiece.

7 Claims, 2 Drawing Sheets

INHALERS

The invention relates to an inhaler for products, such as medicaments, and particularly to an inhaler for transferring to a patient a metered dose of a product contained in a pressurised dispensing container.

In known metered dose inhalers, the aerosol stream from a pressurised dispensing container is fired towards a patient or user of the inhaler into a air flow travelling in the same direction. In known devices, a user inhales through a mouth piece of the inhaler and creates an air flow through the container from air inlet holes which are generally at a part of the inhaler well spaced from the mouth piece. The medicament is then released into this air flow at a point between the air inlet holes and the mouth piece so that it is travelling in the same direction as the air flow. Typically in such devices, there is no restriction in the air flow between the air inlet holes and the mouth piece. Because of this, a substantial air flow may be created by a user of the device and, because the medicament is fired into the air flow in the same direction as the air flow, the effect is that particles of medicament can attain quite substantial velocities. As inhalers of this type are normally designed to be as small as practical for the convenience of users, the distance between the point at which the medicament is fired into the air flow and the patients mouth is usually quite small so that there is little distance to reduce the inertia of the particles of medicament with the result that the particles may impact in the oro-pharynx of a user with quite high velocity. This can be a problem with some medicaments.

In an effort to overcome this problem, devices have been produced in which the medicament is fired into a holding volume which allows the velocity of the medicament to be reduced and also allows some evaporation to occur.

However, these devices with a holding volume tend to be of significantly larger size than the standard metered dose inhalers and therefore less convenient and attractive to users.

A solution to this problem is described in GB-A2279879 describing a reverse flow inhaler in which the air inlet is provided at a location axially between the air outlet of the duct from the medicament container and the mouth piece and a passage is provided connecting the air inlet to a location adjacent the outlet of the duct means. Thus, in use, when a user inhales through the mouth piece, an air flow is created from the inlet means to the mouth piece, the air flow having a component directed away from the mouth piece towards the outlet of the duct means.

This enables the provision of an inhaler which allows delivery of medicament to a user at reduced velocity without significantly increasing the size of the inhaler.

When dispensing products having a low volatility component, such as ethanol, more turbulence is required to achieve sufficient atomization than products having high volatility components. This is best achieved by adding a turbulence generating component in the inhaler. It is vital, however, that because of the nature of use of such inhalers, such components cannot accidentally be dislodged and inhaled by the user.

It is therefore an object of the present invention to provide an inhaler with improved atomization of products.

According to the invention there is provided an inhaler for dispensing a product comprising a housing adapted to receive a pressurised dispensing container, a mouth piece, duct means for connecting an outlet of the container with the mouth piece, air inlet means for allowing air into the inhaler when a user applies suction to the mouth piece, a mechanical break-up component located in the duct means, which component breaks up the product as it passes along the duct means, before mixing with the air flow to effect atomization of the product, in which the duct means include a chamber for receiving the mechanical break-up component, the chamber having an end wall providing a barrier between the chamber and the mouth piece to prevent the mechanical break-up component from entering the mouth piece.

Preferably the mechanical break-up component is substantially cup-shaped.

In a preferred embodiment the duct means further comprises a duct from the container outlet to the chamber and a channel, said channel being positioned so as to communicate with said duct and with a swirl chamber of the mechanical break-up component.

The channel may be formed in the mechanical break-up component.

Preferably the chamber is only accessible via a rear aperture in the housing to insert the mechanical break-up component.

The rear aperture is preferably closed off by means of a removable plug.

The plug preferably provides attachment means for a mouth piece cover to be attached to the housing.

A preferred embodiment of the invention will be described, by way of example only, with reference to the accompanying drawings, in which:

FIG. 1 is a cross-sectional side elevation of an inhaler according to the invention;

FIG. 2 is a cross-sectional elevation of an atomising component of the inhaler of FIG. 1; and FIG. 3 is an end elevation of the atomising component of FIG. 2.

Referring to FIG. 1, an inhaler 10 for a medicament comprises a housing 11 for receiving a pressurised dispensing container 12 of medicament, a mouth piece 14 for insertion into the mouth of a user of the inhaler, and a cover 15 for the mouth piece 14.

The container housing 11 is generally cylindrical and open at its upper end. A lower wall 17 of the housing 11 includes an annular socket 18 for receiving the tubular valve stem 13 of the container 12. The socket 18 communicates with a chamber 19 formed in the housing 11 via a duct 16.

The mouth piece 14, which may be generally circular or shaped to fit the mouth, is connected to the housing 11 through a generally frusto-conical wall portion 20.

FIG. 1 depicts a reverse flow inhaler in which the wall portion 20 includes inner and outer walls 21, 22, the inner wall 21 being an extension of the mouth piece 14 and the outer wall 22 forming with the inner wall a restricted air flow passage from inlet air holes 23 provided in the outer wall around the periphery of the mouth piece to a restricted air inlet 25 adjacent a neck portion 24 of the device. It will be appreciated that the lower wall formation 17 of housing 11 forms a barrier between the open end of the housing 11 and the mouth piece 14 so that there is no air flow passage from around the container 12, or the left side of the housing 11 (as viewed in the drawing), to the mouth piece 14.

The invention may, however, be used in an inhaler with a more traditional air inlet around the sides of the container, or through apertures of the casing 11 elsewhere.

The cover 15 of the device which fits over the open mouth piece 14 is connected by a flexible hinge portion 27 to a cover attachment 28 which fits an aperture 29 in the rear part of the housing 11 to attach the cover 15 to the housing 11.

All of the components of the inhaler 10 may be plastics mouldings.

The chamber 19 communicates with the aperture 29 at one end and with the mouth piece 14 at its other end via an exit orifice 30. The chamber 19 receives a mechanical break-up component 31, which is fitted via the rear aperture 29. The cover attachment 28 plugs the aperture 29 and prevents removal of the component 31.

Figure 2:
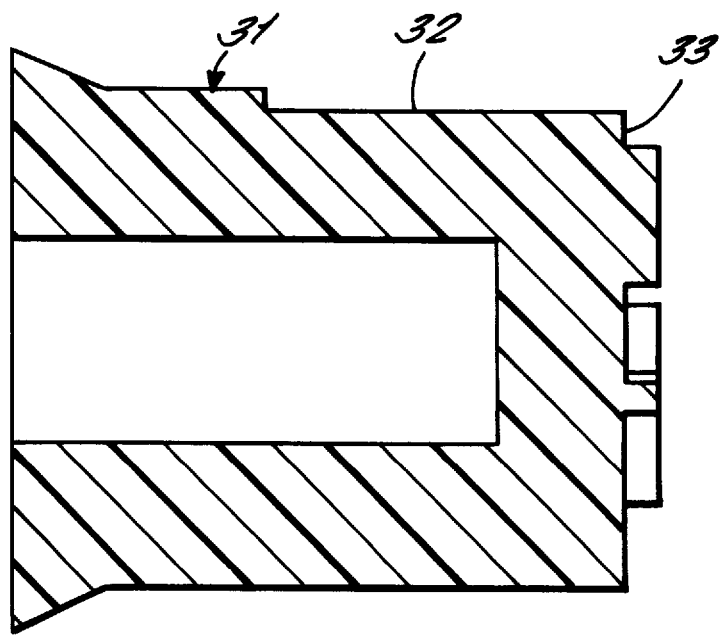
Figure 3:
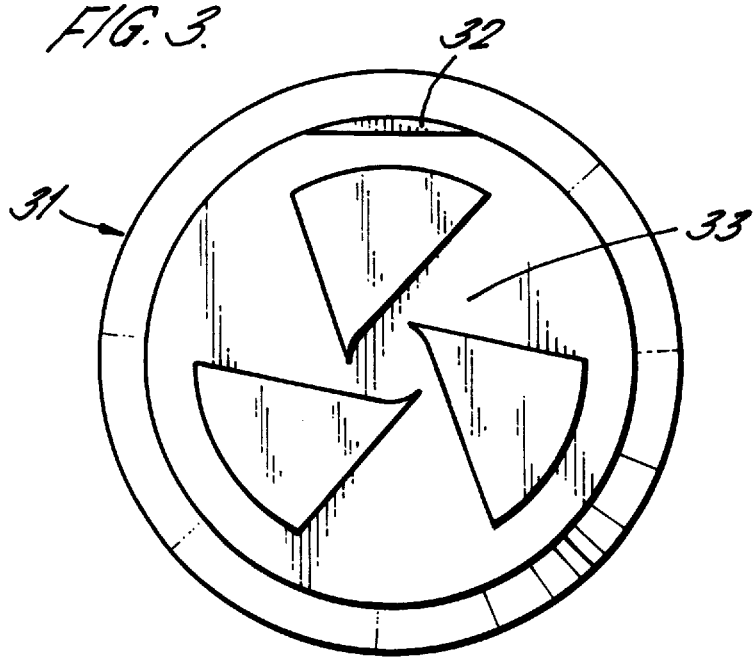

As shown in FIG. 2 the mechanical break-up component 31 is preferably cup-shaped and has a longitudinal groove 32 in its external annular wall, which groove 32 is positioned so as to communicate with duct 16. At the end of the component 31 which is located adjacent the chamber exit orifice 30 there is a swirl chamber 33. The component 31 may, however, be of any appropriate construction to create swirl within the product as it passes through the chamber 19, by bringing in flows from tangential directions.

As the component 31 is located in the chamber 19, the end wall of said chamber 19 in which the exit orifice 30 is located, provides a barrier to prevent the component 31 from being dislodged and being inhaled by the user.

In use, a patient or user holds the inhaler, usually in one hand, and applies his mouth to the mouth piece 14. The user then inhales through the mouth piece 14 and this creates an air flow from inlet air holes 23 via the restricted air inlet 25 to the mouth piece 14. It will be appreciated that the inlet air holes 23 are arranged downstream of the orifice 30 relative to the mouth piece 14, that is to say the inlet air holes 23 are axially closer to the mouth piece 14 than the neck portion 24 and orifice 30. This ensures that when a user inhales through the mouth piece 14, the air flow is not directly from a position upstream of the orifice 30 to the mouth piece 14 but has at least a component of reverse flow towards the orifice 30. The rate of air flow is also controlled by the restricted air inlet 25. The effect of the restriction and the reverse air flow is to create a turbulent air flow in the neck portion 24.

In the alternative embodiments of the invention using non-reverse flow inhalers, the direction of the air flow will of course be different.

After the user has started inhaling through the mouth piece 14, the container 12 is depressed downwardly on to its stem 13 to release a dose of product from the container 12. The dose of product is projected by the pressure in the container 12 through the duct 16 into the chamber 19 around the turbulence generating component 31. The swirl chamber 33 provides a rotational motion to the flow of the product before it leaves the chamber 19 via the exit orifice 30. The turbulent flow of the product then mixes with the turbulent air flow in the mouth piece neck portion 24 to effect atomization of the product which is thence inhaled by the user.

The turbulence of the air flow together with the swirl generated in the product flow ensure that both effective atomization of the product occurs and that the velocity of the particles of the product is relatively low when they enter the oro-pharynx region of the patient.

When not in use, the cover 15 is placed in the position shown in the drawing and when the actuator is to be used, the cover is removed by hinging it away from the mouth piece 14.

The invention is not restricted to the embodiment described above and various modifications may be made within the scope of the appended claims.

I claim:

1. An inhaler for dispensing a product comprising a housing adapted to receive a pressurised dispensing container, a mouth piece, duct means for connecting an outlet of the container with the mouth piece, air inlet means for allowing air into the inhaler when a user applies suction to the mouth piece, a mechanical break-up component located in the duct means, which component breaks up the product as it passes along the duct means, before mixing with the air flow to effect atomization of the product, in which the duct means include a chamber for receiving the mechanical break-up component, the chamber having an end wall providing a barrier between the chamber and the mouth piece to prevent the mechanical break-up component from entering the mouth piece.

2. An inhaler as claimed in claim 1 in which the mechanical break-up component is substantially cup-shaped.

3. An inhaler as claimed in claim 2 in which the duct means further comprises a duct from the container outlet to the chamber and a channel, said channel being positioned so as to communicate with said duct and with a swirl chamber of the mechanical break-up component.

4. An inhaler as claimed in claim 3 in which the channel is formed in the mechanical break-up component.

5. An inhaler as claimed in claim 2 in which the chamber is only accessible via a rear aperture in the housing to insert the mechanical break-up component.

6. An inhaler as claimed in claim 5 in which the rear aperture is closed off by means of a removable plug.

7. An inhaler as claimed in claim 6 in which the plug provides attachment means for a mouth piece cover to be attached to the housing.

* * * * *